United States Patent [19]

Révész et al.

[11] Patent Number: 4,567,192
[45] Date of Patent: Jan. 28, 1986

[54] ACYLAMINOPHENOL DERIVATIVES

[75] Inventors: László Révész, Basel; Trevor J. Petcher, Binningen, both of Switzerland

[73] Assignee: Sandoz Ltd., Basel, Switzerland

[21] Appl. No.: 605,138

[22] Filed: Apr. 30, 1984

[30] Foreign Application Priority Data

May 4, 1983 [CH] Switzerland .......................... 2423/83

[51] Int. Cl.$^4$ .................. C07D 277/56; A01K 31/425
[52] U.S. Cl. ...................................... 514/369; 548/188
[58] Field of Search ......................... 548/188; 424/270; 514/369

[56] References Cited

U.S. PATENT DOCUMENTS 4,181,719  1/1980  Margetts ............................ 424/233
4,335,210  6/1982  Meister et al. ..................... 435/113
4,438,124  3/1984  Meister et al. ..................... 424/270

FOREIGN PATENT DOCUMENTS 1583602  1/1981  United Kingdom ................ 424/233

OTHER PUBLICATIONS

New Scientist, p. 520, Feb. 24, 1983.
Manufacturing Chemist, p. 20, Mar. 1983.
Proc. Nat. Acad. Sci. USA, 78, 936, 1981.
Proc. Nat. Acad. Sci. USA, 79, 6246, 1982.

Primary Examiner—Robert Gerstl
Attorney, Agent, or Firm—Gerald D. Sharkin; Robert S. Honor; Thomas O. McGovern

[57] ABSTRACT

Compounds of formula I

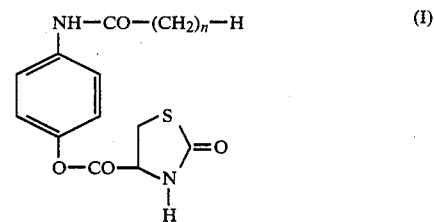

wherein $n=1$ to 5 possessing analgesic activity with reduced hepatoxicity as compared with paracetamol.

6 Claims, No Drawings

ACYLAMINOPHENOL DERIVATIVES

The present invention relates to novel acylaminophenol derivatives having valuable pharmaceutical properties as well as to processes for the production of these derivatives, pharmaceutical compositions comprising them, and their use as pharmaceuticals.

British patent specification No. 1,583,602 discloses a class of N-acetylaminothioalkanoic acid ester derivatives of N-acetyl-para-aminophenol which have analgesic activity while being relatively free from hepatoxic effect when taken in overdose. The present invention relates to a novel class of acylaminophenol esters including novel esters of N-acetyl-para-aminophenol [N-(4-hydroxyphenyl)acetamide or paracetamol] in which the ester moiety is structurally entirely distinct from that of the said prior art proposal and which have also been found to exhibit analgesic activity with relative freedom from hepatoxic effect when taken in overdose. The derivatives of the invention may be shown to have advantageous pharmacological properties, e.g. yet further improved tolerability, compared with the aforementioned known derivates.

More particularly the present invention provides a compound of formula I

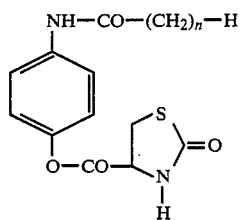

wherein n is an integer of from 1 to 5 inclusive.

In the compounds of formula I, n is preferably 1.

As will be appreciated the compounds of the invention contain an asymmetric carbon atom and accordingly exist in both racemic as well optically active isomeric form. The present invention is to be understood as including both individual D- and L-optically active isomers of the compounds of the invention as well as mixtures thereof. The L-isomers are preferred.

The present invention also provides a process for the production of a compound of formula I, which process comprises reacting a compound of formula II

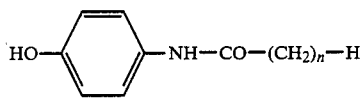

wherein n has the meaning given for formula I, with 2-oxo-thiazolidine-4-carboxylic acid or a reactive derivative thereof.

Suitable reactive derivatives of 2-oxo-thiazolidine-4-carboxylic acid are e.g. the acyl halides in particular chlorides. Reaction is suitably carried out in the presence of an inert solvent or diluent such as acetonitrile and/or dimethylformamide, e.g. in the presence of an acid binding agent such as pyridine at e.g. $-10°$ C. to ambient temperature. The starting materials for use in the above process are known or may be prepared in accordance with known techniques.

Optically active isomers of the compounds of formula I may be prepared directly by use of the appropriate optically active starting material, e.g. (L)-2-oxo-thiazolidine-4-carboxylic acid or a reactive derivative thereof to obtain the L-isomer product, or by resolution of initially obtained racemic mixtures in accordance with standard techniques.

The following example is illustrative of the process for the production of the compounds of the invention.

EXAMPLE

Preparation of (4-Acetamido-phenyl)-2-oxo-thiazolidine-4-carboxylate 0.85 ml oxalyl chloride are added at $-10°$ C. to a mixture of 10 ml acetonitrile and 2.2 ml dimethylformamide and the whole is stirred for 15 minutes before combining with 1.3 g (L)-2-oxo-thiazolidine-4-carboxylic acid. After a further 15 mins. 3.3 g N-(4-hydroxyphenyl)acetamide in 2.2 ml pyridine are added dropwise at $-10°$ C. The reaction mixture is warmed to room-temperature and stirred over-night. The obtained precipitate is filtered off, washed with tetrahydrofuran and recrystallised from acetonitrile to yield the title compound in the form of its L-isomer: m.p.=204°-205° C.

The compounds of the invention exhibit valuable pharmaceutical, in particular analgesic, properties as shown in standard tests for example:

(I) The arthritis pain test (based on the method of A. W. Pircio et al., Eur. J. Pharmacol. 31, 207–215, 1975); and (II) The Randall-Selitto Test on the inflamed rat hind-paw (Arch. Int. Pharmacodyn. 61, 409–419, 1957).

Compounds in accordance with the present invention are active in test I above at dosages in the range of from 150 to 300 mg/kg body weight p.o. and in test II above at dosages of from 200 to 500 mg/kg body weight p.o.

The compounds of the invention are accordingly useful as analgesics, e.g. in the treatment of pain of varying aetiology. For this use the dosage will of course vary depending on the specific compound employed, the mode of administration, the condition to be treated and the specific treatment desired. In general however satisfactory results are obtained on administration of compounds of formula I at a daily dosage of from about 15 to about 300 mg/kg body weight, administered orally once, in divided dosages 2 to 4 times a day or in sustained release form. For larger mammals the total daily dosage is in the range of from about 1 to about 4 g and dosage forms for oral administration suitably comprise from about 250 mg to about 2 g of compound of formula I together with a pharmaceutically acceptable diluent or carrier therefor.

As previously indicated, required daily dosages will depend inter al. on the particular compound of the invention employed. Results obtained for the the compounds (L)-(4-acetamido-phenyl)-2-oxo-thiazolidine-4-carboxylate (compound A) in accordance with the present invention and the known analgesic paracetamol (compound B) in tests I and II above are shown in the following table.

|  |  | $ED_{50}$ (mg/kg p.o.) | |
|---|---|---|---|
|  |  | COMPOUND A | COMPOUND B |
| Test I | 1 hr. | ca. 162 | 75 |
|  | 3 hrs. | 162 | 142 |
|  | 5 hrs. | 264 | 261 |

| | ED$_{50}$ (mg/kg p.o.) | |
|---|---|---|
| | COMPOUND A | COMPOUND B |
| Test II | 310 | 203 |

Dosages of COMPOUND A required for the treatment of pain will accordingly generally be of the order of from 1 to 1.5 times those required using conventional paracetamol therapy.

As is well known in the art, when paracetamol is taken in high dosages extensive damage of the liver is caused and this may lead to death. In accordance with the present invention it has surprisingly be found that compounds of formula I exhibit greatly reduced hepatoxicity compared with paracetamol, as may be shown by determination of GOT (Glutamate-Oxalacetate-Transaminase) and GPT (Glutamate-Pyruvate-Transaminase) levels in mouse serum (c.f. "Remmington's Pharmaceutical Sciences" (1980), 544–545 and Jungermann and Möhler, "Biochemie", Springer Verlag (1980), 555). Thus on administration of 1'000 mg/kg p.o. of COMPOUND A in accordance with the invention to mice, no increase in GOT and GPT levels over levels in untreated controls (40 to 80 units/liter) is observed and no deaths are recorded. In contrast on administration of compound B (paracetamol) at a dosage of 560 mg/kg p.o., GOT levels are elevated to 3'800 units/liter and GPT levels are elevated to 3'000 units and on administration of compound B at a dosage of 1'000 mg/kg p.o., death of 2 out of 5 test animals is recorded.

Thus, for the compounds of the invention, risk of death via drug abuse, e.g. in the event of attempted suicide, is accordingly greatly reduced as compared with risk for the known analgesic paracetamol. The compounds of the invention thus provide much "safer" medicaments, with reduced risk or danger of abuse.

In accordance with the foregoing the present invention also provides:

(I) A pharmaceutical composition comprising a compound of formula I as hereinbefore defined together with a pharmaceutically acceptable diluent or carrier therefor;

(II) A compound of formula I as hereinbefore defined for use as a pharmaceutical, e.g. for use an analgesic; and (III) A method of treating pain in a subject in need of such treatment, which method comprises administering to said subject an analgesically effective amount of a compound of formula I as hereinbefore defined.

We claim:

1. A compound of formula I

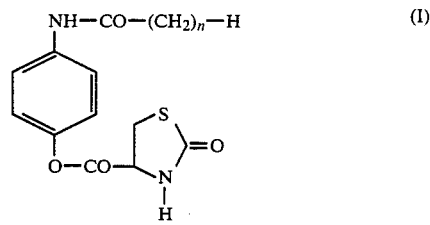

wherein n is an integer of from 1 to 5.

2. A compound according to claim 1 wherein n is 1.

3. A compound according to claim 1 which is the L-isomer.

4. A compound according to claim 1 which is (L)-(4-Acetamidophenyl)-2-oxo-thiazolidine-4-carboxylate.

5. A pharmaceutical composition useful in treating pain comprising an analgesic effective amount of a compound as defined in claim 1 together with a pharmaceutically acceptable diluent or carrier therefor.

6. A method of treating pain in a subject in need of such treatment, which method comprises administering to said subject an analgesically effective amount of a compound as defined in claim 1.

* * * * *